United States Patent [19]

Schulz

[11] Patent Number: 4,782,502
[45] Date of Patent: Nov. 1, 1988

[54] FLEXIBLE CALIBRATION PHANTOM FOR COMPUTER TOMOGRAPHY SYSTEM

[76] Inventor: Eloy E. Schulz, 25010 Daisy Ave., Loma Linda, Calif. 92354

[21] Appl. No.: 914,170

[22] Filed: Oct. 1, 1986

[51] Int. Cl.⁴ .................. A61B 6/02; G01N 23/00
[52] U.S. Cl. ............................... 378/18; 378/207; 250/252.1
[58] Field of Search ............... 378/18, 207; 250/252.1; 338/212

[56] References Cited

U.S. PATENT DOCUMENTS

| | | |
|---|---|---|
| 4,053,781 | 10/1977 | Hounsfield ........................... 378/18 |
| 4,115,691 | 9/1978 | Oldendorf . |
| 4,124,799 | 11/1978 | Schittenhelm . |
| 4,233,507 | 11/1980 | Volz . |
| 4,651,335 | 3/1987 | Kalender et al. ................... 378/207 |

FOREIGN PATENT DOCUMENTS

| | | |
|---|---|---|
| 55-129037 | 10/1980 | Japan ................................. 378/18 |
| 402070 | 4/1974 | U.S.S.R. ......................... 250/252.1 |
| 425146 | 9/1974 | U.S.S.R. . |
| 903192 | 6/1960 | United Kingdom ................ 378/207 |

OTHER PUBLICATIONS

White, D. R., "Tissue Substitutes in Experimental Radiation Physics", Med. Phys., 5(6), Nov./Dec., 1978, pp. 467–478.

Banzer, D., U. Schneider and O. Wegener, Vertebral Mineral by CT Scanning.

Revak, Conrad S., G. H. Alexander, May 1980. A Method for Densitometry of Cortical Bone by Computed Tomography, Proceedings, Fourth International Conference on Bone Measurement, NIH Publication No. 80-1938, May 1980, pp. 242–252.

Revak, Conrad S., 1980. Mineral Content of Cortical Bone Measured by Computed Tomography, Journal of Computer Assisted Tomography, Jun., 4(3): 342–350.

White, D. R., R. J. Martin, and R. Darlison, 1977, Epoxy Resin.

Based Tissue Substitutes, British Journal of Radiology, 50:814–821, Proceedings of CT Densitometry Workshop, Journal Computer Assisted Tomography, vol. 3, No. 6, 1979.

Primary Examiner—Craig E. Church
Assistant Examiner—T. N. Grigsby
Attorney, Agent, or Firm—Kelly, Bauersfeld & Lowry

[57] ABSTRACT

In a computer tomography system, a flexible calibration phantom is utilized simultaneously with analysis of a patient to ensure accuracy of imagry and to facilitate interpretation of tomographs created. The flexible calibration phantom is preferably placed directly upon a patient between a radiation source and a radiation detector. It includes two solid and flexible samples of reference materials, each having a substantially uniform density, and a solid and flexible encasement surrounding the samples of reference material. The encasement has a substantially uniform density different than that of each of the samples of reference material, and the combination provides suitable reference points for proper analysis of tomographs obtained.

18 Claims, 2 Drawing Sheets

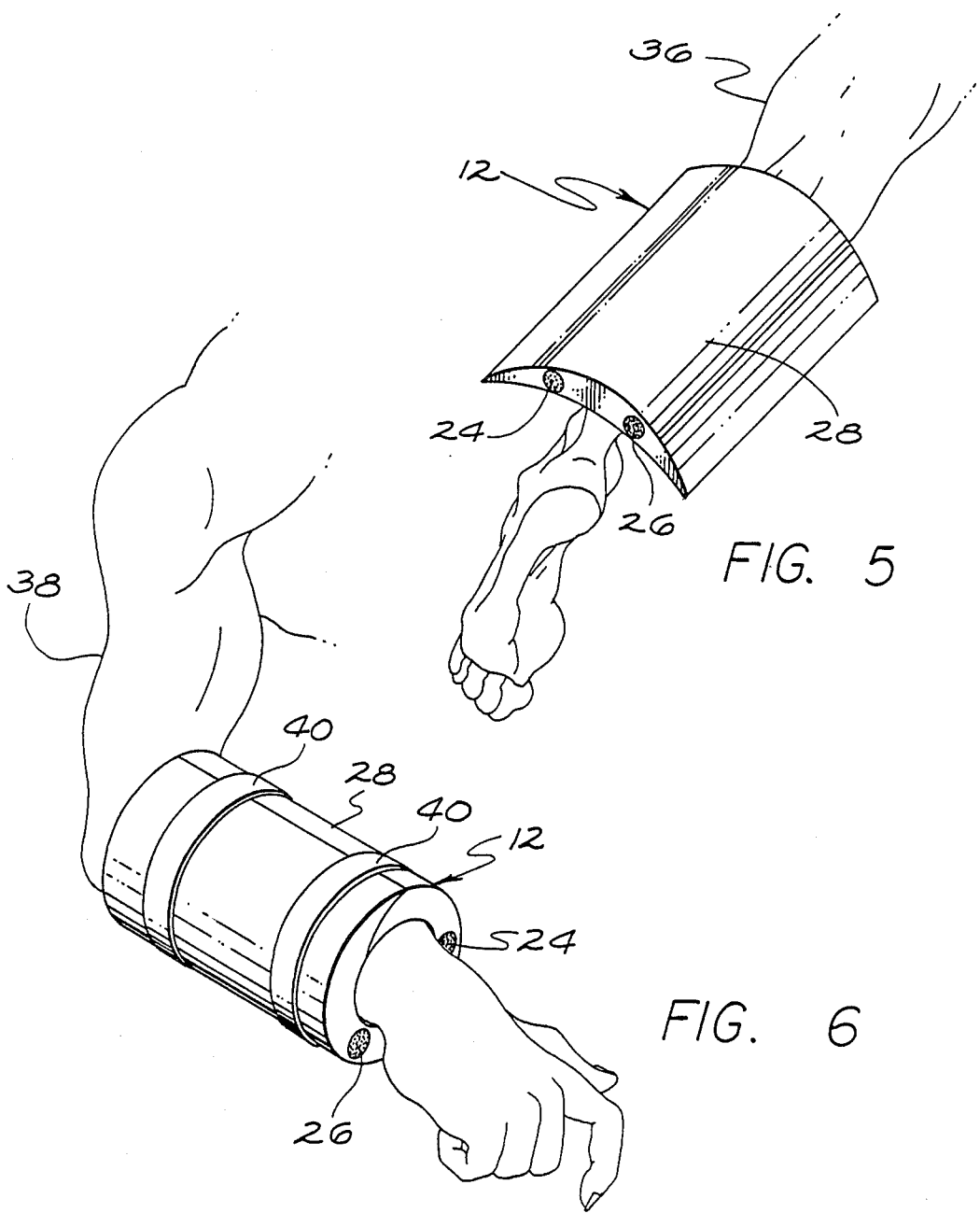

FLEXIBLE CALIBRATION PHANTOM FOR COMPUTER TOMOGRAPHY SYSTEM

BACKGROUND OF THE INVENTION

This invention relates generally to computed tomography systems, and, more specifically, to flexible calibration phantoms which are scanned simultaneously with a portion of a body in connection with analysis of patients utilizing such systems.

In a common method of computed tomography, a patient is supported for translational movement along a longitudinal axis which coincides with the center of rotation of a gantry having an X-ray source on one side of the center of rotation and an X-ray detector on the other side. A pencil-like or fan-shaped X-ray beam is projected through the patient as the gantry rotates so that the detector may develop signals indicative of X-ray transmission characteristics along a plurality of paths through the patient. Analog signals representative of X-ray attenuation by all of the volume elements in a layer of the patient at various rotational angles are then converted to digital signals which are used by a computer to produce signals that may thereafter be used to produce a reconstructed image of the layer. The reconstructed image of the radiation attenuation coefficients may be displayed in gray tones on the screen of a visual display or on developed film.

One of the primary problems associated with computed tomography systems is proper calibration. The computer tomography system is quite complex and subject to occasional interference and signal drift which may result in a slight shift in performance. Another problem associated with system calibration is due to a phenomenon referred to as "beam hardening". The radiation attenuation coefficient is a property of every material and expresses the radiation absorption properties of the material at a specific X-ray energy.

The attenuation coefficients and corresponding gray tones produced by the computed tomography system are relative and must be calibrated to known values. Some systems are calibrated on a regular basis by scanning a set of known reference samples mounted in what is referred to as a calibration phantom. Prior art phantoms are available in a number of variations, some being plastic replicas of the human body, or specific portions thereof, while others consist of actual human bones cast in plastic. Some phantoms include a set of reference samples having known attenuation coefficients surrounded by a water medium housed within a plastic vessel.

Phantoms can also be used to correlate images from calibrated machines to analyze and interpret the images. In order to facilitate use of a phantom simultaneously with the analysis of a patient, a tabletop has been designed which includes a sample of reference material positioned to appear in each computed tomograph image. Such a computer tomography table containing calibration and correlation samples is shown in U.S. Pat. No. 4,233,507, the contents of which are incorporated herein.

In some instances it is desirable to place the phantom on or wrap it about a body part to be examined. Prior phantoms used simultaneously with the analysis of the patient, however, generally include a rigid encasement which holds a plurality of fluid-containing tubes, forming a tabletop upon which the patient lies. These rigid phantoms are considered unacceptable for regular use outside of the tabletop. Further, prior phantoms incorporating fluid reference samples often have air bubbles within the samples which can interfere with proper system calibration.

Accordingly, there has been a need for a novel calibration phantom which may be easily and comfortably placed directly on a body part to be examined, which also has sufficient flexibility to conform to normal body contours and thus eliminate air gaps between the body and the phantom. Additionally, there exists a need for a calibration phantom which utilizes soft and flexible samples of reference materials for reliable calibration of systems simultaneously with analysis of the patient. Moreover, a calibration phantom is needed which is relatively inexpensive to produce, durable, and capable of use in most existing computed tomography systems. The present invention fulfills these needs and provides other related advantages.

SUMMARY OF THE INVENTION

The present invention resides in a novel flexible calibration phantom for use in a computed tomography system. The flexible calibration phantom is intended to be placed directly upon a patient between a radiation source and a radiation detector, and utilized simultaneously during analysis of the patient. The radiation source includes means for projecting penetrating radiation through a slice of the body of the patient along a plurality of substantially linear paths. The radiation detector includes means for detecting the radiation emergent from the body along each of the paths and for producing output signals indicative of the absorption suffered by the radiation on traversing the paths.

In a preferred form of the invention, the flexible calibration phantom includes two flexible samples of reference material, each having a substantially uniform density, and a flexible encasement surrounding the samples of reference material. The samples of reference material are disposed parallel to one another within the encasement, and the samples of reference material, as well as the encasement, each have properties which correspond to known radiation attenuation coefficients.

A first one of the samples of reference material is preferably formed, at least in part, with a tri-basic calcium hydroxide material to have a density approaching that of bone in humans. The encasement, on the other hand, is preferably formed of a PVC material. The second sample of reference material is constructed to have a density approximately equivalent to that of water, by mixing PVC material with phenolic microspheres.

The flexible calibration phantom of the present invention can be economically molded utilizing known procedures. As shown in the accompanying drawings, the flexible calibration phantom can be molded so the upper surface of the encasement forms a circular-like arc, and the lower surface thereof forms an elliptical-like arc. Due to the nature of the materials used, the calibration phantom easily conforms to the normal contours of the body, and may be wrapped about a body part and/or attached thereto by any suitable means, i.e., straps, tape, etc.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 4 is an enlarged sectional view taken along the line 4—4 of FIG. 2, illustrating the manner in which a pair of solid and flexible samples of reference material are disposed within a solid and flexible encasement;

FIG. 5 is a perspective view illustrating the manner in which the flexible calibration phantom may be utilized in connection with analysis of a patient's extremity in a computed tomography system; and FIG. 6 illustrates the manner in which the flexible calibration phantom can be dimensioned for complete encirclement of a portion of the body, and further the manner in which the phantom can be securely attached to the patient.

DETAILED DESCRIPTION OF THE PREFERRED EMBODIMENT

Figure 1:
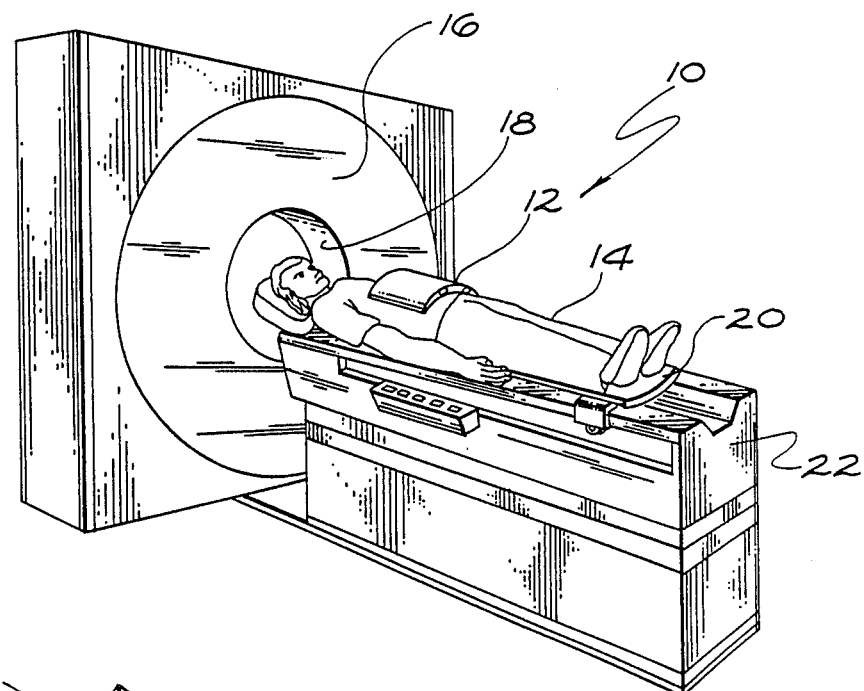
FIG. 1 is a perspective view of a patient undergoing computed tomography analysis, and the flexible calibration phantom of the present invention is shown positioned over the patient's abdominal area.

As shown in the drawings for purposes of illustration, the present invention is concerned with a computed tomography system, generally designated in the accompanying drawings by the reference number 10, and a flexible calibration phantom 12 for use in such a system. Referring initially to FIG. 1, there is shown a patient 14 in position for analysis by the computed tomography system 10. X-ray scanning and the acquisition of X-ray attenuation data on a multitude of small volume elements of the patient 14 is carried out with components of a gantry, which is generally designated by the reference number 16. The gantry 16 is generally vertical and has a cylindrical horizontal opening 18 for receiving the patient 14 for examination. The details of the gantry 16 are described in U.S. Pat. No. 4,093,860, entitled "Gantry For Computed Tomography" by Kelman, et al., the contents of which are incorporated herein by reference. The details of the gantry 16 are not shown, but generally include an X-ray source and collimator on one side of the opening 18 which project a thin, pencil-like or fan shaped beam of radiation which is received by an X-ray detector on the opposite side of the opening. A suitable detector is shown in U.S. Pat. No. 4,031,396 to Whetten, et al., also incorporated by reference herein.

The patient 14 is supported in the opening 18 by a tabletop 20, which is translatable in the longitudinal direction along a base 22. The tabletop 20 is preferably constructed utilizing composite structure techniques which provide very high strength and very low X-ray absorption. The discrete plurality of analog signals representative of X-ray attenuation by small volume elements in the patient are processed in a data acquisition system, after which the analog signals are converted to digital signals which are used by a computer to execute an image reconstruction algorithm. The above-described computed tomography system 10 is generally known in the art.

Figure 2:
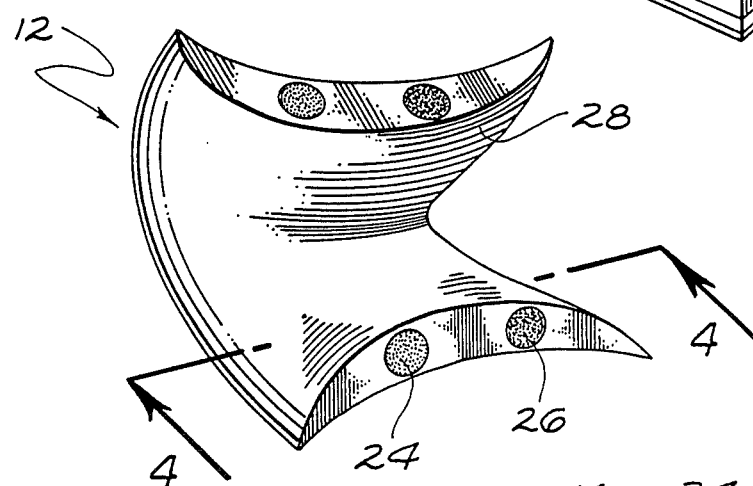
FIG. 2 is a perspective view of the flexible calibration phantom of the present invention, illustrated in a bent configuration to show the flexibility of the various components thereof.
Figure 3:
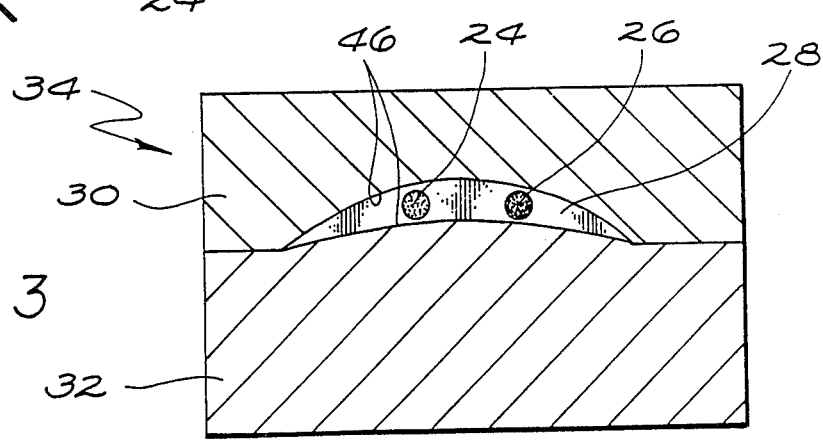
FIG. 3 is a sectional view of a molding apparatus for forming the flexible calibration phantom of the present invention, the upper mold plate including a circular-like arc, and the lower mold plate including an elliptical-like arc for forming the exterior surfaces of the phantom.

In accordance with the present invention, and as best illustrated in FIGS. 2-4, the flexible calibration phantom 12 includes, generally, two solid and flexible cores or samples of reference material 24 and 26, surrounded by a molded solid and flexible encasement 28. The cores 24 and 26 are preferably formed of solid plastic materials and shaped to resemble rod-like cylinders. While each of these cores 24 and 26 are alike in that they each have a substantially uniform density throughout, they are different in that the density of each core is different from the other.

In forming the flexible calibration phantom 12 of the present invention, the cores 24 and 26 are disposed parallel to one another between two plates 30 and 32 of a mold 34, and a plastic-like material is injected between the mold plates in a manner surrounding the cores. This material, when set up, forms the encasement 28, and it too is preferably formed of a material having a substantially uniform density throughout.

It is presently preferred that the materials forming the cores 24 and 26, and the encasement 28, all have properties which correspond to known radiation attenuation coefficients. In this regard, the first core or sample of reference material 24 is formed, at least in part, with a tri-basic calcium hydroxide material having a density approaching that of bone in humans. The encasement is preferably formed of a PVC (Polyvinyl Chloride) material sold under the trade name HAFLEX by Hastings Plastics of Santa Monica, Calif. The second core or sample of reference material 26 is preferably formed of a mixture of the HAFLEX PVC material and phenolic microspheres to create a mixture having a density approximately equivalent to that of water. It has been found that the particular combination of materials described above closely approximates the densities of body portions analyzed in computed tomography applications, and therefore they provide good reference points for analysis of images obtained.

These particular materials also, when combined as illustrated and described above, give mechanical flexibility to the calibration phantom 12 which enables its use upon virtually any portion of the patient as required in a myriad of computed tomography applications. For example, as illustrated in FIGS. 5 and 6, the flexible calibration phantom 12 may be conveniently placed over any one of the patient's extremities, such as a leg 36 or an arm 38. Moreover, because of the flexibility afforded by the nature of the calibration phantom 12 described above, it can be flexed sufficiently to wrap completely around a patient's arm 38 or the like. When so used, the phantom 12 can be securely affixed to the patient by tape 40 (as illustrated in FIG. 6), or any other suitable means.

In order to facilitate placement of the flexible calibration phantom 12 upon the patient 14, it has been found advantageous to form the encasement 28 to have an upper-surface 42 in the shape of a circular-like arc, and further to have a lower surface 44 in the shape of an elliptical-like arc. This is easily accomplished by simply appropriately configuring the facing surfaces 46 of the upper and lower plates 30 and 32 of the mold 34 as illustrated in FIG. 3.

From the foregoing it is to be appreciated that the flexible calibration phantom 12 provides a relatively inexpensive, durable apparatus for use simultaneously with the analysis of the patient in a computed tomography system, and eliminates disadvantages attendant to use of rigid encasements which typically held a plurality of fluid-containing tubes forming the tabletop upon which the patient was supported. More particularly, the use of soft and flexible samples of reference materials (the cores 24 and 26) eliminates the problems which can occur when air bubbles are present in fluid samples. Moreover, the flexible calibration phantom of the present invention, when placed directly upon a patient between the radiation source and the radiation detector, conforms to normal body contours and thus avoids the appearance of air gaps between the phantom and the patient which could occur with prior art phantoms. Additionally, it has been found that because the phantom 12 is relatively comfortable for the patient 14, displacement of the phantom 12 with respect to the patient (which occurs with prior art phantoms when the patient moves or dislodges the phantom), is almost entirely avoided.

Although a particular embodiment of this invention has been described in detail for purposes of illustration, various modifications may be made without departing from the spirit and scope of the invention. Accordingly, the invention is not to be limited, except as by the appended claims.

I claim:

1. A process for examining a body with X-rays and generating a computer tomograph, the steps comprising:

placing a flexible calibration phantom adjacent the body, the phantom including a flexible sample of solid reference material of substantially uniform X-ray density and a flexible encasement of solid material surrounding the sample of reference material, the encasement having a substantially uniform X-ray density different than that of the sample of reference material, the degree of flexibility of the phantom being such that when the flexible calibration phantom is placed adjacent a selected portion of the body, the phantom adapts substantially in shape to the anatomical contours in response to no more force than its own weight;

projecting X-rays through a slice of the body; and detecting the X-rays emergent from the body for producing output signals indicative of the absorption suffered by the X-rays.

2. A process as set forth in claim 1, wherein the phantom is placed directly upon the body.

3. A system for examining a body with X-rays and generating a computer tomograph, comprising:

means for scanning a spacial region into which the body to be examined can be brought, from numerous angular positions with an irradiating beam of X-rays;

radiation detector means disposed in a centered or aligned fashion on the opposite side of the spacial region for supplying measured attenuation coefficients for the individual radiation paths; and flexible calibration phantom means introduced into the spacial region to be scanned by said beam, which phantom means includes a plurality of solid and flexible samples of reference material each having a different substantially uniform X-ray density, and a solid and flexible encasement of reference material surrounding the plurality of samples, wherein the encasement has a substantially uniform X-ray density different than that of at least two of the samples;

the degree of flexibility of the phantom being such that when the flexible calibration phantom is placed adjacent a selected portion of the patient's body, the phantom adapts substantially in shape to the anatomical contours in response to no more force than its own weight.

4. A system as set forth in claim 3, wherein the samples of reference material and the encasement each have properties which correspond to known radiation attenuation coefficients.

5. A system as set forth in claim 3, wherein a first sample of reference material has an X-ray density approaching that of bone in humans, and a second sample of reference material has an X-ray density approximately equivalent to that of water.

6. A system as set forth in claim 5, wherein the first sample of reference material is formed, at least in part, with a tri-basic calcium hydroxide material, the encasement is formed of a PVC material, and the second sample of reference material is formed of a mixture of PVC material and phenolic microspheres.

7. A tomography system, comprising:

source means for projecting X-rays through a slice of the body of a patient along a plurality of substantially linear paths;

detector means for detecting the radiation emergent from the body along each of said paths and for producing output signals indicative of the absorption suffered by the radiation on traversing the paths; and flexible calibration phantom means disposed adjacent the body between the source means and the detector means, the phantom means including a first flexible sample of solid reference material of substantially uniform X-ray density, and a solid and flexible encasement surrounding the sample of reference material, the encasement having a substantially uniform X-ray density different than that of the sample of reference material;

the degree of flexibility of the phantom being such that when the flexible calibration phantom is placed adjacent a selected portion of the patient's body, the phantom adapts substantially in shape to the anatomical contours in response to no more force than its own weight.

8. A system as set forth in claim 7, including means for attaching the flexible calibration phantom means to the body.

9. A system as set forth in claim 7, wherein the first sample of reference material has an X-ray density approximately equal to that of water.

10. A system as set forth in claim 7, wherein the first sample of reference material has an X-ray density approaching that of bone in humans.

11. A system as set forth in claim 10, wherein the first sample of reference material is formed, at least in part, with a tri-basic calcium hydroxide material.

12. A system as set forth in claim 7, wherein the encasement is formed of a PVC material.

13. A system as set forth in claim 12, wherein the first sample of reference material is formed of a mixture of the material forming the encasement and phenolic microspheres.

14. A system as set forth in claim 7, including a plurality of flexible samples of reference material.

15. A system as set forth in claim 14, wherein an upper surface of the encasement forms a circularlyshaped arcuate surface, and a lower surface thereof forms an elliptically-shaped arcuate surface.

16. A system as set forth in claim 15, wherein the encasement is sufficiently large to be able to wrap about a body part.

17. A system as set forth in claim 14, including a second flexible sample of reference material disposed parallel to the first sample of reference material within the encasement, the second sample of reference material having a substantially uniform X-ray density different than those of the first sample of reference material and the encasement.

18. A system as set forth in claim 17, wherein the samples of reference material and the encasement each have properties which correspond to known radiation attenuation coefficients.

* * * * *